(12) United States Patent
Wang et al.

(10) Patent No.: US 10,258,379 B2
(45) Date of Patent: Apr. 16, 2019

(54) MANDIBULAR FIXATION DEVICE

(71) Applicant: METAL INDUSTRIES RESEARCH & DEVELOPMENT CENTRE, Kaohsiung (TW)

(72) Inventors: Yue-Jun Wang, Kaohsiung (TW);
Tung-Lin Tsai, Kaohsiung (TW);
Chun-Chieh Tseng, Kaohsiung (TW);
Li-Wen Weng, Kaohsiung (TW);
Chih-Lung Lin, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 32 days.

(21) Appl. No.: 15/373,653

(22) Filed: Dec. 9, 2016

(65) Prior Publication Data
US 2018/0161068 A1  Jun. 14, 2018

(51) Int. Cl.
*A61B 17/66* (2006.01)
*A61B 17/68* (2006.01)

(52) U.S. Cl.
CPC ...... *A61B 17/663* (2013.01); *A61B 2017/681* (2013.01)

(58) Field of Classification Search
CPC . A61B 17/663; A61B 17/666; A61B 17/6433; A61B 17/8071; A61C 5/88; A61C 5/80; A61C 8/003
See application file for complete search history.

(56) References Cited

U.S. PATENT DOCUMENTS

| | | | |
|---|---|---|---|
| 6,302,687 B1 * | 10/2001 | King | A61B 17/663 433/18 |
| 8,414,581 B2 | 4/2013 | Shah et al. | |
| 8,662,889 B2 | 3/2014 | Baker | |
| 2002/0018978 A1 * | 2/2002 | Triaca | A61B 17/663 433/7 |
| 2004/0088054 A1 * | 5/2004 | Berry | A61F 2/4455 623/17.11 |
| 2004/0102776 A1 * | 5/2004 | Huebner | A61B 17/1728 606/281 |
| 2010/0274248 A1 * | 10/2010 | Overes | A61B 17/7059 606/71 |

* cited by examiner

*Primary Examiner* — Julianna N Harvey
(74) *Attorney, Agent, or Firm* — Alan D. Kamrath; Kamrath IP Lawfirm, P.A.

(57) ABSTRACT

A mandibular fixation device overcomes the low operability of the conventional mandibular fixation device. The mandibular fixation device includes a sleeve, a first screw rod, a second screw rod and two positioning members. The sleeve includes two ends respectively provided with first and second screw holes. The first and second screw holes have opposite spiral directions. The first screw rod has a first threaded portion and a first assembly portion. The first threaded portion is threadedly engaged with the first screw hole, and the first assembly portion is located outside of the sleeve. The second screw rod has a second threaded portion and a second assembly portion. The second threaded portion is threadedly engaged with the second screw hole, and the second assembly portion is located outside of the sleeve. The two positioning members are coupled with the first and second assembly portions, respectively.

9 Claims, 8 Drawing Sheets

MANDIBULAR FIXATION DEVICE

BACKGROUND OF THE INVENTION

1. Field of the Invention

The present disclosure generally relates to a medical instrument and, more particularly, to a mandibular fixation device configured to fix the mandible of the patient in place during mandibular reconstruction surgery.

2. Description of the Related Art

After an accidental oral injury, if the patient suffers from a serious mandibular fracture or undergoes a cutting procedure that cuts a part of the mandible of the patient and adversely causes a wide range of a fracture or bone defect, the patient would require mandibular reconstruction surgery to rebuild the facial outline and chewing function. In the case where the mandible is completely broken, the mandible would displace under the pulling of the masseter muscle and tongue muscle. In light of this, repositioning surgery is needed to place the mandible back to the original position, and internal fixation is required to fix the mandible in place. However, since the face has extremely complex blood vessel, nerve and muscle systems, if the repositioning surgery is not precisely carried out, some sequelaes such as facial numbness, malocclusion, jaw joint stiffness, and facial asymmetry may result. Facial defects will also affect the patient's confidence in socialization and may cause depression.

In order to smoothly perform mandibular reconstruction surgery, repositioning surgery is needed to fix the maxilla and mandible in the normal positions where the occlusion is proper. After the reconstruction surgery, the devices that are used to fix the maxilla and mandible are removed. In modern clinically mandibular reconstruction surgery, there are two approaches of fixation: (1) manual fixation and (2) intermaxillary fixation. In the manual fixation, the surgeon simply uses his/her hands to reconstruct the mandible of the patient (using prosthesis). However, this approach simply relies on the skill of the surgeon without any aid to precisely fix the mandible. In the intermaxillary fixation, the dental arch bars are respectively fixed to the teeth of the maxilla and mandible, or a plurality of bone nails is drilled into the gums of the maxilla and mandible. Then, steel wires or rubber bands are used to fix the mandible in place. As such, the maxilla and mandible can remain in the normal positions where the occlusion is proper.

For example, U.S. Pat. No. 8,414,581 discloses an intermaxillary fixation device. A zip tie is tied around the gap between two teeth. The upper and lower arch bars are fixed to the upper and lower rows of teeth, respectively. Then, the upper and lower arch bars are tied by several zip ties to attain the positioning effect. The conventional intermaxillary fixation device can advantageously prevent the steel wire from hurting the patient or the surgeon. However, the operation of the intermaxillary fixation device is complex and time-consuming, so that it is not suitable for the patient with larger teeth gaps or with some teeth missing. U.S. Pat. No. 8,662,889 discloses another conventional maxillary fixation device. In such a device, the upper and lower dental arch bars are respectively fixed to the upper and lower gums with a plurality of bone nails. Then, each corresponding pair of the hooks is tied together by a steel wire. This maxillary fixation device is suitable for the patient with larger teeth gaps or with some teeth missing. However, the use of a large quantity of bone nails not only creates many wounds and increases the risk of infection, but also requires the surgeon to check if there is any bone nail that hurts the root and nerve of the tooth. Thus, the operation is more complex and time-consuming, and the steel wire may still hurt the patient and the surgeon.

SUMMARY OF THE INVENTION

To solve the problem, the disclosure provides a mandibular fixation device which efficiently and accurately positions the mandible of the patient with a proper positioning member according to the condition of the mandible (e.g. depending on the degree of injury to the mandible, whether the patient has no teeth, and whether the patient has teeth but the tooth gaps are larger than normal).

In an embodiment, a mandibular fixation device including a sleeve, a first screw rod, a second screw rod and two positioning members is provided. The sleeve includes two ends respectively provided with a first screw hole and a second screw hole. The first screw hole has a spiral direction opposite to a spiral direction of the second screw hole. The first screw rod has a first threaded portion and a first assembly portion. The first threaded portion is threadedly engaged with the first screw hole, and the first assembly portion is located outside of the sleeve. The second screw rod has a second threaded portion and a second assembly portion. The second threaded portion is threadedly engaged with the second screw hole, and the second assembly portion is located outside of the sleeve. The two positioning members are coupled with the first and second assembly portions, respectively.

Based on this, the mandibular fixation device of the disclosure can efficiently and accurately position the mandible of the patient with a proper positioning member according to the condition of the mandible (e.g. depending on the degree of injury to the mandible, whether the patient has no teeth, and whether the patient has teeth but the tooth gaps are larger than normal). Thus, the efficiency in retaining the mandible of the patient is largely improved, permitting the surgeon to focus on the reconstruction of the mandible. Thus, the surgeon does not need to spend a lot of effort and time in retaining the mandible of the patient. This not only reduces the complexity of the surgery and the surgery time, but also ensures a proper positioning effect of the mandible. As such, the mandible of the patient can remain in a normal position after the surgery, increasing the confidence of the patient in socialization.

The first screw hole is coaxial with the second screw hole.

The first screw hole has a same thread pitch as the second screw hole. This structure permits the first and second screw rods to move in the same speed and distance.

The sleeve has a central portion in a form of a hexagonal prism. The structure is easy for processing and formation and can reduce the possibility that the hand of the user slides off the sleeve when holding and operating the sleeve.

Each of the two positioning members includes a ring body and a rotating member. The rotating member includes a first end that is fixed to the first assembly portion of the first screw rod or the second assembly portion of the second screw rod. The rotating member includes a second end rotatably connected to the ring body. This structure permits the ring body to be rotated and smoothly fitted around the tooth of the patient according to the angle of the tooth.

The ring body is in a form of a C-shaped ring having an opening. This structure allows the ring body to have a high elasticity so that the ring body can be easily fitted around or removed from a tooth of the patient.

The rotating member includes an upper screwing tab and a lower screwing tab. The upper screwing tab has a through-hole, and the lower screwing tab has a screwing hole. The first assembly portion of the first screw rod or the second assembly portion of the second screw rod is in a form of a protruding ring and extends into a space between the upper screwing tab and the lower screwing tab. A screw extends through the through-hole of the upper screwing tab and the first or second assembly portion, and is threadedly engaged with the screwing hole of the lower screwing tab. The structure is simple and easy for manufacturing and assembly, thereby reducing the manufacturing cost and improving convenience in assembly.

Each of the two positioning members includes a connection portion and a plurality of screwing portions. The connection portion is fixed to the first assembly portion of the first screw rod or the second assembly portion of the second screw rod. The plurality of screwing portions is connected to the connection portion and includes a plurality of through-holes. This structure allows the mandibular fixation device to be used in a situation where the patient has no teeth or the patient has teeth but the tooth gaps are larger than normal.

The connection portion includes an upper screwing tab and a lower screwing tab. The upper screwing tab includes a through-hole, and the lower screwing tab includes a screwing hole. The first assembly portion of the first screw rod or the second assembly portion of the second screw rod is in a form of a protruding ring and extends into a space between the upper screwing tab and the lower screwing tab. A screw extends through the through-hole of the upper screwing tab and the first or second assembly portion, and is threadedly engaged with the screwing hole of the lower screwing tab. The structure is simple and easy for manufacturing and assembly, thereby reducing the manufacturing cost and improving convenience in assembly.

The first assembly portion is mounted to one of two axial ends of the first screw rod. The first screw rod has a maximal diameter between the first threaded portion and another of the two axial ends of the first screw rod. The second assembly portion is mounted to one of two axial ends of the second screw rod. The second screw rod forms a channel in an open state at another of the two axial ends of the second screw rod. The channel has a minimal diameter larger than the maximal diameter of the first screw rod. This structure can increase the range of the relative telescopic movement between the first and second screw rods as controlled by the sleeve.

The first and second screw rods have a same structure. In this arrangement, it is not required to separately manufacture and pack the first and second screw rods. It is also not necessary to classify the first and second screw rods during the assembly thereof, attaining convenient manufacturing, warehousing and assembly.

The first assembly portion is mounted to one of two axial ends of the first screw rod. Another of the two axial ends of the first screw rod forms a first stopper portion. The first threaded portion is located between the first assembly portion and the first stopper portion. The first stopper portion has a flat end face.

BRIEF DESCRIPTION OF THE DRAWINGS

The present disclosure will become more fully understood from the detailed description given hereinafter and the accompanying drawings which are given by way of illustration only, and thus are not limitative of the present disclosure, and wherein.

Figure 1:
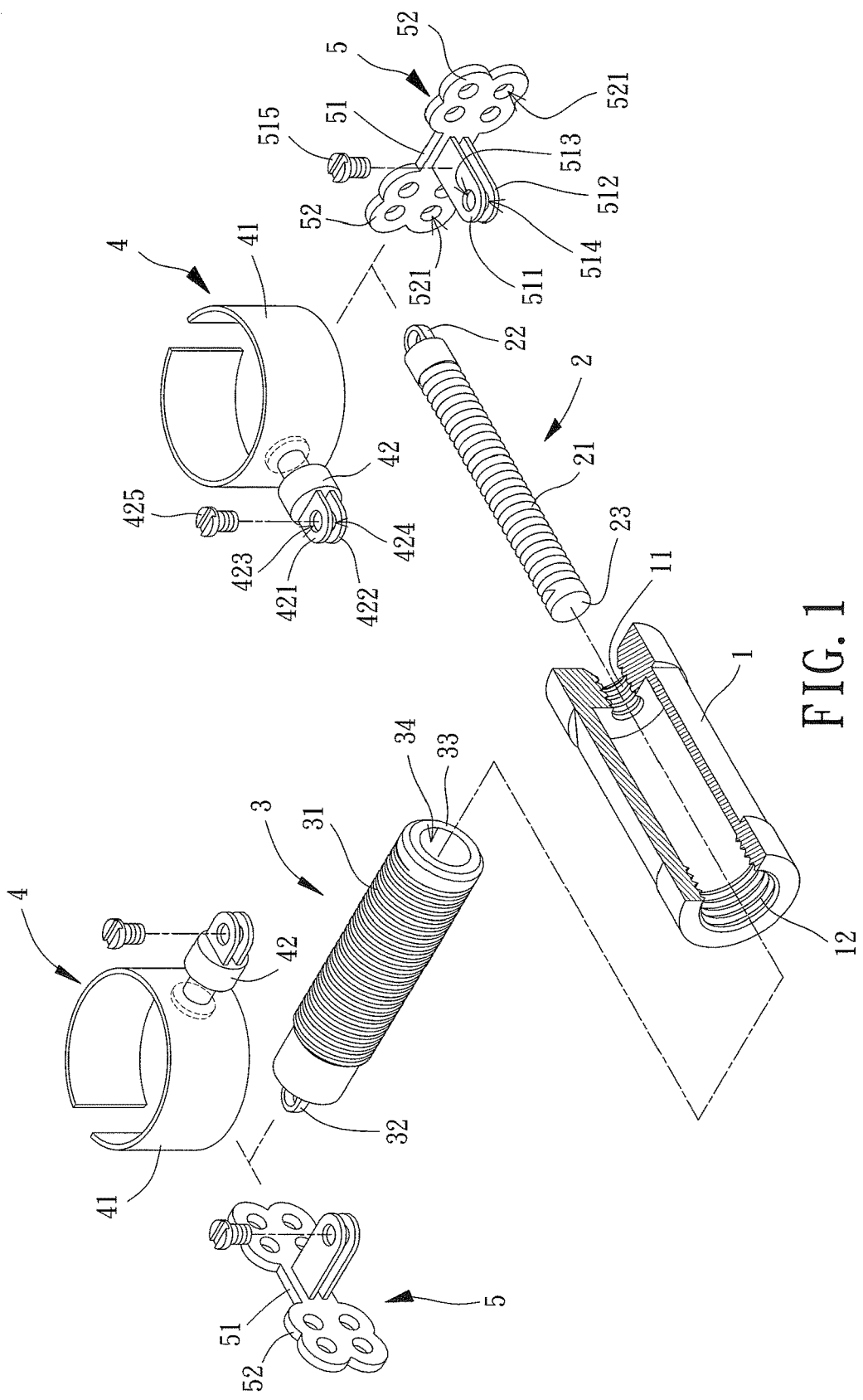
FIG. 1 is an exploded view of a mandibular fixation device according to a first embodiment of the disclosure.

In the various figures of the drawings, the same numerals designate the same or similar parts. Furthermore, when the terms "first", "second", "third", "fourth", "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the disclosure.

DETAILED DESCRIPTION OF THE INVENTION

FIG. 1 shows a mandibular fixation device according to a first embodiment of the disclosure. The mandibular fixation device can be made of pure titanium (such as Ti6Al4V, TiNi, Ti15Mo), medical-use stainless steel (such as 304, 316, 410 types) or cobalt-chrome-molybdenum alloy, and is formed by at least one of the processes including 3D printing technology, CNC machining, casting, and wire electrical discharge machining. The mandibular fixation device generally includes a sleeve 1, a first screw rod 2, a second screw rod 3 and two positioning members. The first and second screw rods 2 and 3 are screwed to the sleeve 1. The two positioning members are exposed outside of the sleeve 1 and coupled with the first and second screw rods 2 and 3, respectively. In the embodiment, the positioning member is implemented as a dental ring 4 or a bone plate 5, but is not limited thereto.

The sleeve 1 is hollow and includes two ends spaced from each other in an axial direction. The sleeve 1 includes a first end provided with a first screw hole 11 into which the first screw rod 2 is screwed, as well as a second screw hole 12 into which the second screw rod 3 is screwed. The sleeve 1 can be turned to move the first and second screw rods 2 and 3 toward each other or away from each other synchronously. The sleeve 1 is not limited to any shape. The sleeve 1 can be in the form of a cylinder with a non-smooth surface so that the hand of the user will not easily slide off the sleeve 1 when holding and operating the sleeve 1. However, in a non-limited example, the central portion of the sleeve 1 can be in a hexagonal shape that is simple and easily formed.

It is noted that the first screw hole 11 has a spiral direction opposite to the spiral direction of the second screw hole 12. Namely, when the first screw hole 11 has a left-hand inner thread, the second screw hole 12 has a right-hand inner thread. To the contrary, when the first screw hole 11 has a right-hand inner thread, the second screw hole 12 has a left-hand inner thread. Furthermore, the first screw hole 11 is preferably coaxial with the second screw hole 12. The first screw hole 11 may have the same thread pitch as the second screw hole 12, such that the first and second screw rods 2 and 3 can have the same movement speed and can be spaced from the center of the sleeve 1 at the same distance.

Figure 3:
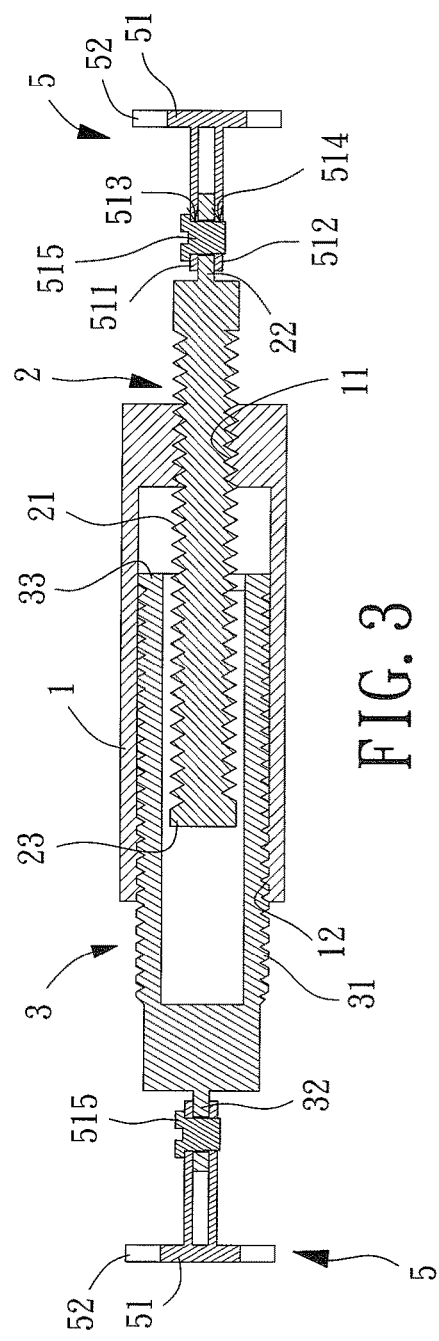
FIG. 3 is a cross sectional view of the mandibular fixation device of the first embodiment where the first screw rod extends into the second screw rod.

Referring to FIGS. 1 and 3, the first and second screw rods 2 and 3 can have the same or different structures according to the requirement. In the embodiment, one of the first screw rod 2 and the second screw rod 3 can have a larger diameter, and another of the first screw rod 2 and the second screw rod 3 can have a smaller diameter. Thus, when the first screw rod 2 and the second screw rod 3 approach each other, the screw rod with the smaller diameter can extend into the screw rod with the larger diameter to increase the range of the relative telescopic movement between the two screw rods.

Figure 2:
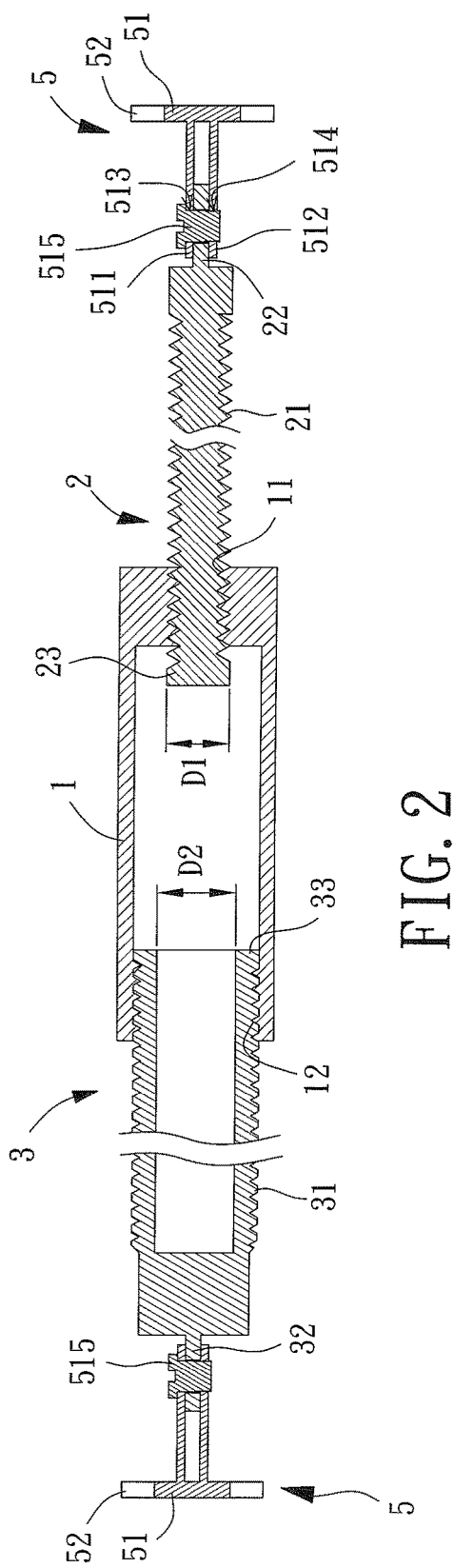
FIG. 2 is a cross sectional view of the mandibular fixation device of the first embodiment where the first screw rod does not extend into the second screw rod.

Specifically, the first screw rod 2 includes a first threaded portion 21 and a first assembly portion 22. The first screw rod 2 is engaged with the first screw hole 11 via the first threaded portion 21 while the first assembly portion 22 is located outside of the sleeve 1. As such, one of the dental ring 4 and the bone plate 5 can be attached to the first assembly portion 22. In FIGS. 2 and 3, the first assembly portion 22 is shown to be connected by the bone plate 5. In the embodiment, the first assembly portion 22 may be mounted to one of two axial ends of the first screw rod 2, and is in the form of a protruding ring. Another of the two axial ends of the first screw rod 2 forms a first stopper portion 23, and the first threaded portion 21 is located between the first assembly portion 22 and the first stopper portion 23. The first screw rod 2 has a maximal diameter D1 between the first threaded portion 21 and the first stopper portion 23.

Similarly, the second screw rod 3 includes a second threaded portion 31 and a second assembly portion 32. The second screw rod 3 is engaged with the second screw hole 12 via the second threaded portion 31 while the second assembly portion 32 is located outside of the sleeve 1. As such, another dental ring 4 or bone plate 5 can be attached to the second assembly portion 32. In FIGS. 2 and 3, the second assembly portion 32 is shown to be connected by the bone plate 5. In the embodiment, the second assembly portion 32 may be mounted to one of two axial ends of the second screw rod 3, and is in the form of a protruding ring. Another of the two axial ends of the second screw rod 3 forms a second stopper portion 33, and the second threaded portion 31 is located between the second assembly portion 32 and the second stopper portion 33. The main difference between the second screw rod 3 and the first screw rod 2 is that the interior of the second screw rod 3 forms a channel 34. The channel 34 is in an open state at the second stopper portion 33 and has a minimal diameter D2. The minimal diameter D2 is larger than the maximal diameter D1 of the first screw rod 2.

Based on this, referring to FIG. 3, when the sleeve 1 is turned to synchronously move the first screw rod 2 and the second screw rod 3 toward each other, the first screw rod 2 and the second screw rod 3 will still move further after the first stopper portion 23 and the second stopper portion 33 pass the same radial plane. This permits the first threaded portion 21 and the first stopper portion 23 to extend into the channel 34 of the second screw rod 3, thereby controlling the range of the relative telescopic movement between the first screw rod 2 and the second screw rod 3.

Figure 4A:
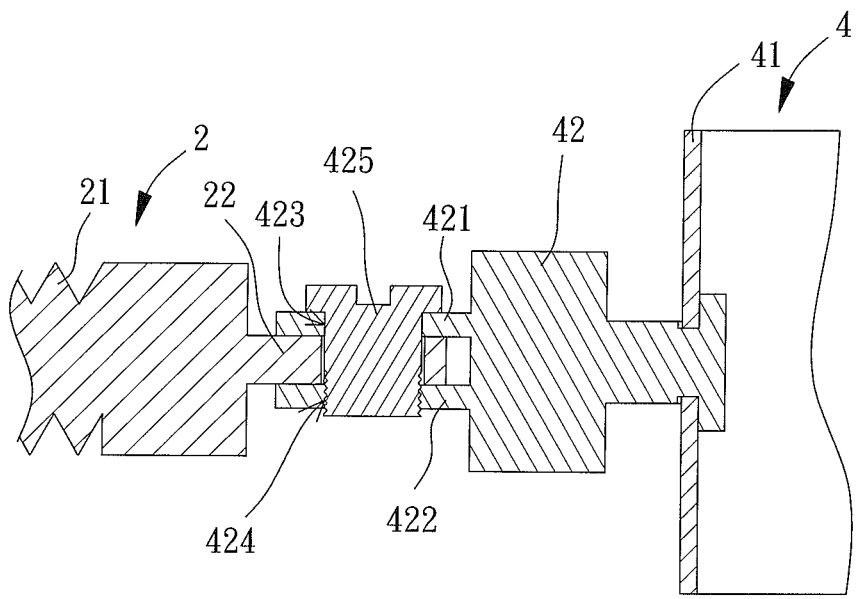
FIG. 4a is a partial, cross sectional view of the mandibular fixation device coupled with a dental ring according to the first embodiment of the disclosure.

Referring to FIGS. 1 and 4a, the dental ring 4 includes a ring body 41 and a rotating member 42. The ring body 41 may be in a form of a C-shaped ring having an opening, such that the ring body 41 can have a high elasticity. As such, the ring body 41 can be fitted around or removed from a tooth of the patient. The rotating member 42 may have a first end that can be coupled to the first assembly portion 22 of the first screw rod 2 or the second assembly portion 32 of the second screw rod 3. Based on this, the rotating member 42 and the first screw rod 2 (or the second screw rod 3) can have a complete immovable state having zero freedom of movement therebetween. The rotating member 42 may have a second end rotatably connected to the ring body 41, permitting the ring body 41 to be rotated and smoothly fitted around the tooth of the patient according to the angle of the tooth.

In a non-limiting example, the rotating member 42 in the embodiment includes one end distant to the ring body 41. Said end of the rotating member 42 includes an upper screwing tab 421 and a lower screwing tab 422. The upper screwing tab 421 has a through-hole 423, and the lower screwing tab 422 has a screwing hole 424. The first assembly portion 22 of the first screw rod 2 is in the form of a protruding ring, and may extend into the space between the upper screwing tab 421 and the lower screwing tab 422. A screw 425 extends through the through-hole 423 of the upper screwing tab 421 and the first assembly portion 22, and is threadedly engaged with the screwing hole 424. Thus, one end of the rotating member 42 is fixed to the first assembly portion 22 of the first screw rod 2. For the other dental ring 4, the rotating member 42 is also similar and is fixed to the second assembly portion 32 of the second screw rod 3. In another embodiment, the end of the rotating member 42 that is fixed to the first screw rod 2 or the second screw rod 3 may be a single-axis joint, an universal joint, a ball joint with a quick-release screw rod, or a threadedly clamping or pushing structure.

Figure 4B:
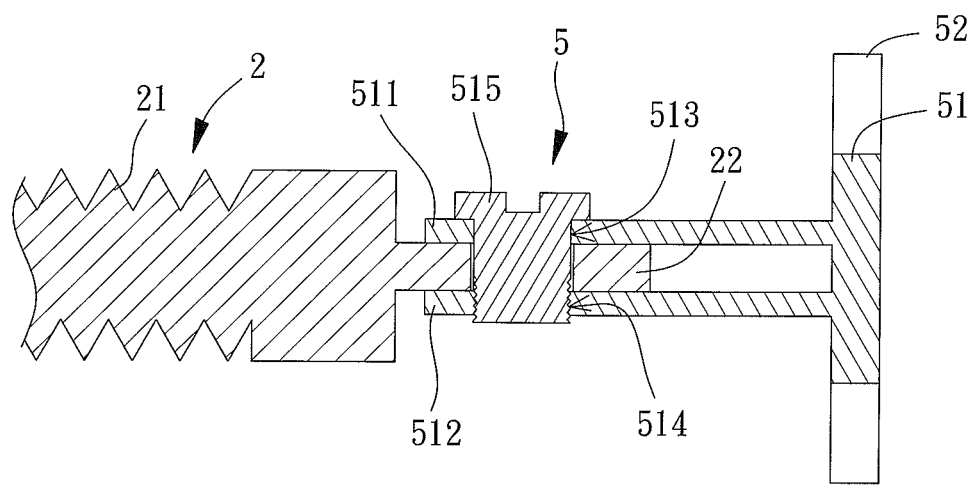
FIG. 4b is a partial, cross sectional view of the mandibular fixation device coupled with a bone plate according to the first embodiment of the disclosure.

Referring to FIGS. 1 and 4b, the bone plate 5 includes a connection portion 51 and a plurality of screwing portions 52. The connection portion 51 can be fixed to the first assembly portion 22 of the first screw rod 2 or the second assembly portion 32 of the second screw rod 3, presenting a complete immovable state having zero freedom of movement between the connection portion 51 and the first screw rod 2 (or the second screw rod 3). Each of the plurality of screwing portions 52 is connected to the connection portion 51 and includes a plurality of through-holes 521 through which a plurality of bone nails (not shown) can extend.

In a non-limiting example, the connection portion 51 includes one face provided with an upper screwing tab 511 and a lower screwing tab 512. The upper screwing tab 511 and the lower screwing tab 512 are spaced from each other in a longitudinal direction. The upper screwing tab 511 includes a through-hole 513, and the lower screwing tab 512 includes a screwing hole 514. The first assembly portion 22 of the first screw rod 2 is in the form of a protruding ring, and may extend into the space between the upper screwing tab 511 and the lower screwing tab 512. Then, after the angle of the bone plate 5 relative to the first screw rod 2 is adjusted, another screw 515 extends through the through-hole 513 of the upper screwing tab 511 and the first assembly portion 22, and is threadedly engaged with the screwing hole 514 of the lower screwing tab 512. Thus, the connection portion 51 can be fixed to the first assembly portion 22 of the first screw rod 2 while the bone plate 5 remains at a predetermined angle relative to the first screw rod 2. For the other bone plate 5, the connection portion 51 also has a similar structure and can be fixed to the second assembly portion 32 of the second screw rod 3. In another embodiment, the connection portion 51 may be a single-axis joint, an universal joint, a ball joint with a quick-release screw rod, or a threadedly clamping or pushing structure.

Figure 5:
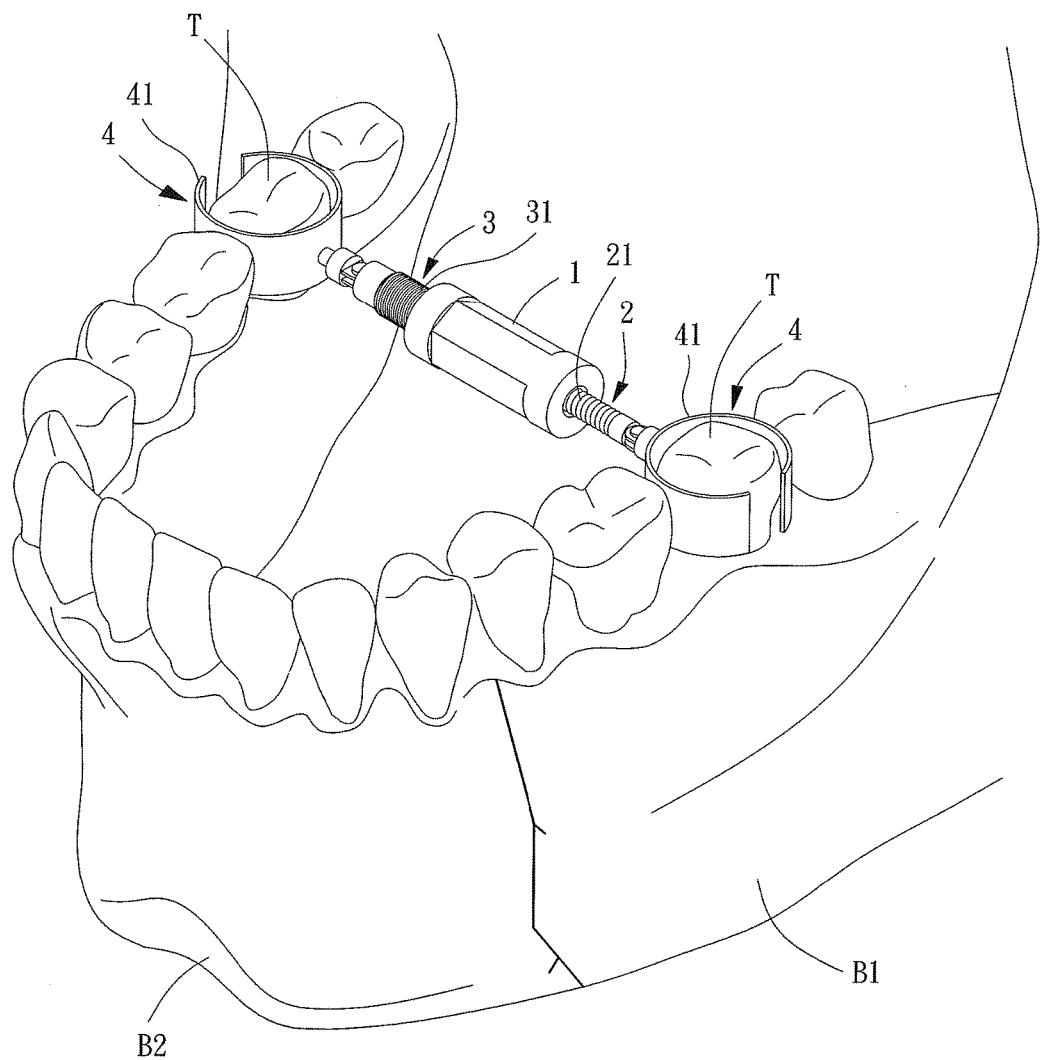
FIG. 5 shows the use of the mandibular fixation device in reconstruction of the cracked mandible of the patient where the teeth are still present.

Based on the structure shown in FIG. 5, when the mandibular fixation device of the disclosure is used in mandibular reconstruction surgery, if the mandible of the patient cracks but the teeth still exist without large teeth gaps, two dental rings 4 can be coupled with the first screw rod 2 and the second screw rod 3, respectively. Then, the sleeve 1 can be turned to keep the two dental rings 4 from each other for a proper distance. If the mandible of the patient cracks into two parts B1 and B2, each of the dental rings 4 can be fitted around a tooth T of a respective part B1 or B2. As such, the two cracked parts B1 and B2 can be accurately and completely fixed in position for the subsequent debridement process and mandibular reconstruction surgery.

Figure 6:
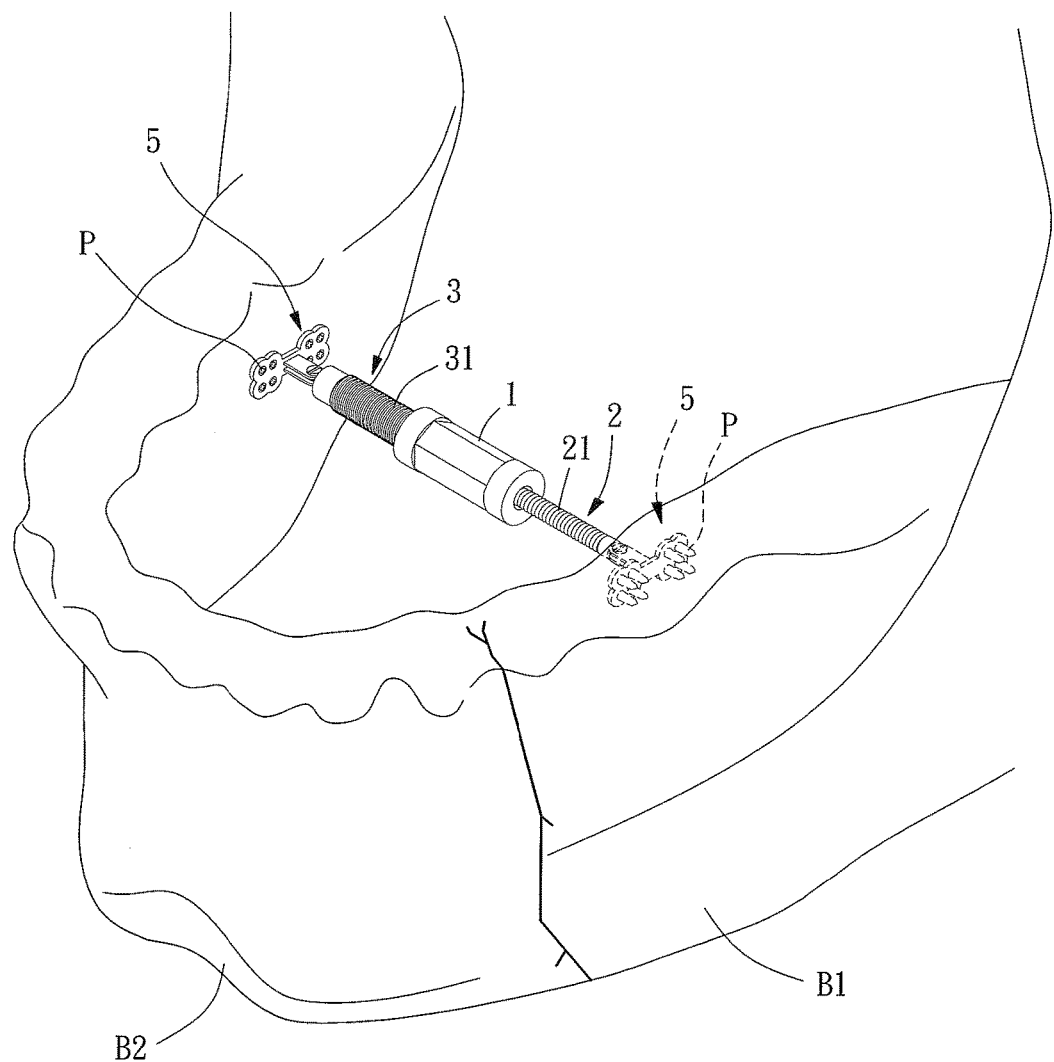
FIG. 6 shows the use of the mandibular fixation device in reconstruction of the cracked mandible of the patient where the patient has no teeth.

Referring to FIG. 6, if the patient has no teeth, it would be impossible to position the dental rings 4 since the use of the dental rings 4 requires the teeth as shown in FIG. 4. If the patient has larger teeth gaps, the dental ring 4 will loosen and cannot be stably positioned. At this time, two bone plates 5 can be used. The two bone plates 5 can be coupled with the first screw rod 2 and the second screw rod 3, respectively. Then, the sleeve 1 can be turned to keep the two bone plates 5 from each other for a proper distance, and a plurality of bone nails P can be used to screw the two bone plates 5 to the inner sides of the breaking parts B1 and B2. As such, the two breaking parts B1 and B2 can be accurately and completely fixed in position for the subsequent debridement process and mandibular reconstruction surgery.

Figure 7:
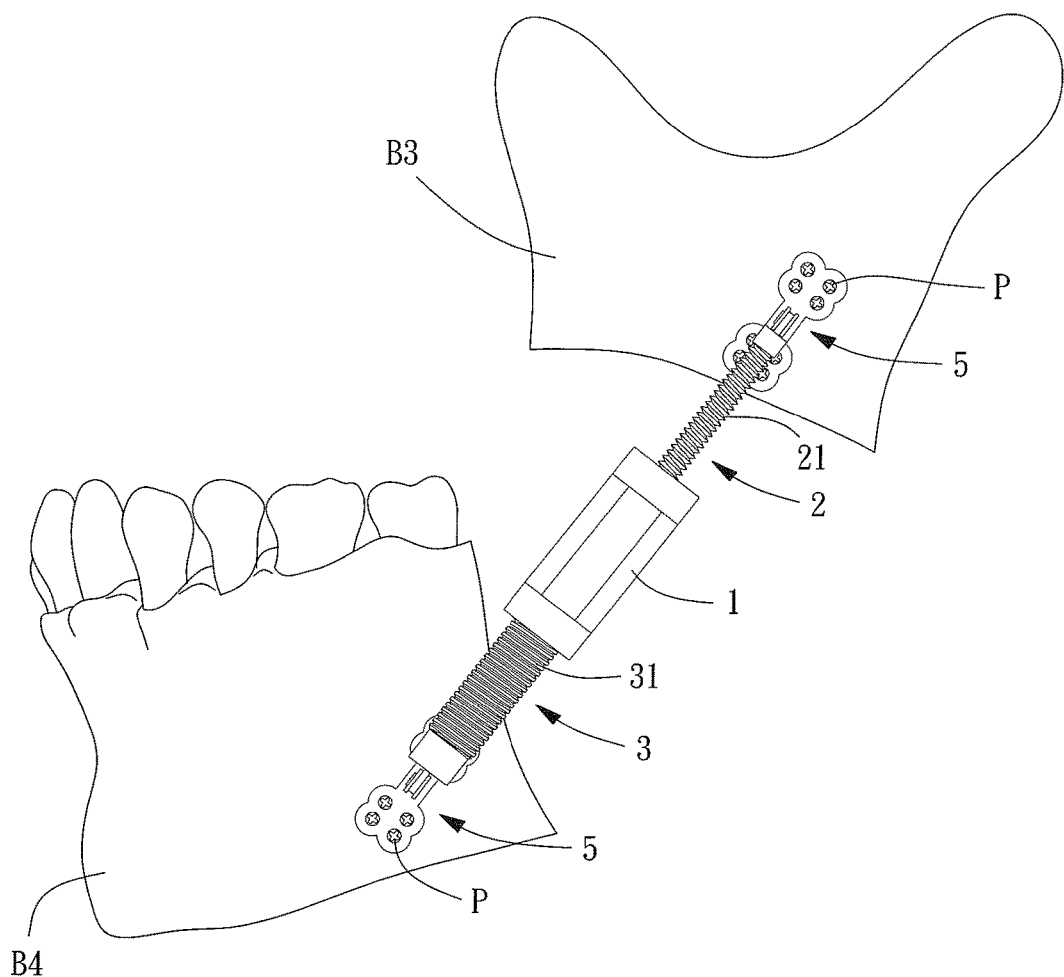
FIG. 7 shows the use of the mandibular fixation device in reconstruction of the broken mandible of the patient.

Referring to FIG. 7 where some part of the mandible is missing and the mandible only has a first remaining part B3 and a second remaining part B4. In this situation, the two bone plates 5 can be coupled with the first screw rod 2 and the second screw rod 3, respectively. Then, the sleeve 1 can be turned to keep the two bone plates 5 from each other for a proper distance, and a plurality of bone nails P can be used to screw the two bone plates 5 to the same side of the remaining parts B3 and B4. As such, the two remaining parts B3 and B4 can be accurately and completely fixed in position for the subsequent debridement process and mandibular reconstruction surgery.

Figure 8:
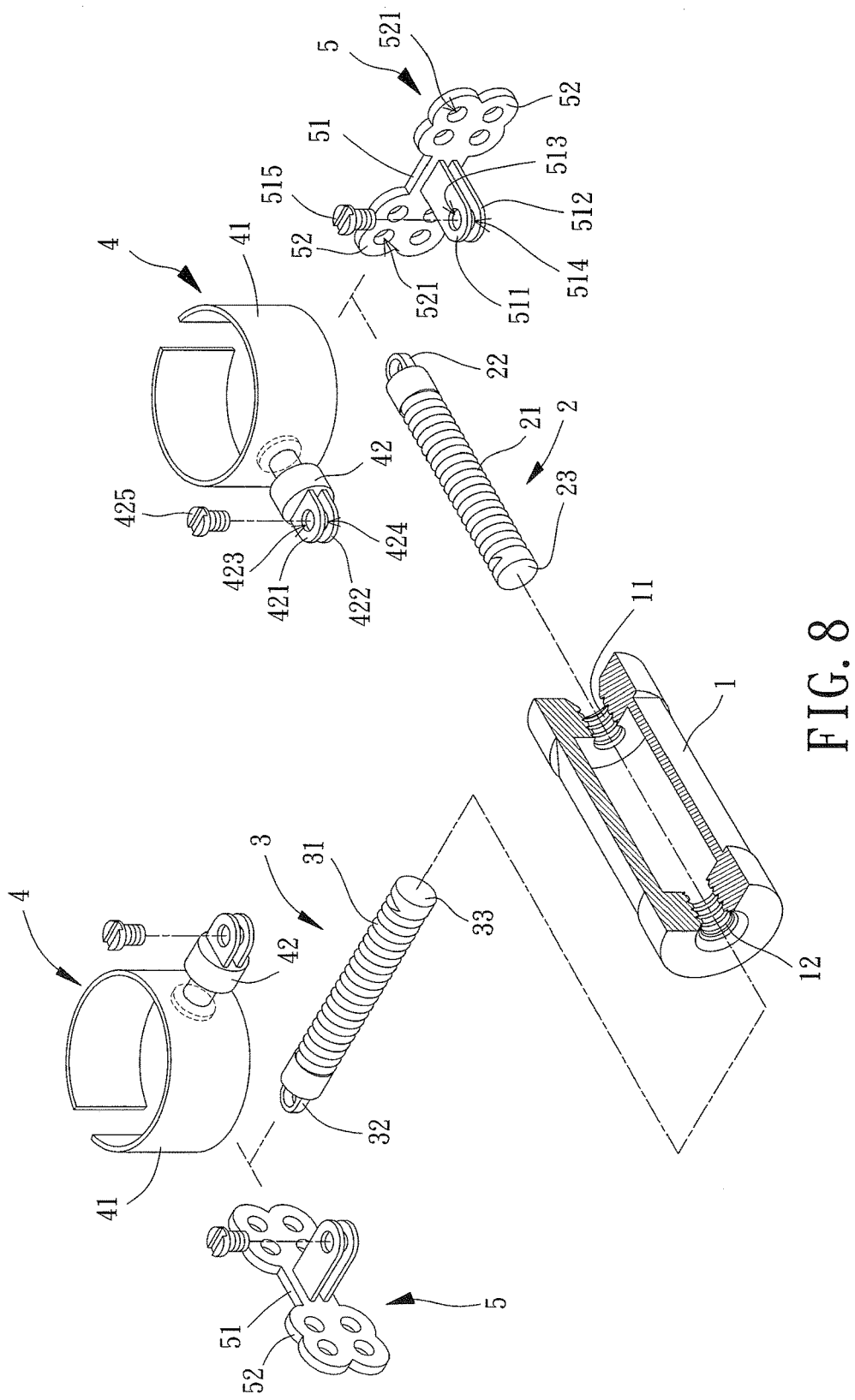
FIG. 8 is an exploded view of a mandibular fixation device according to a second embodiment of the disclosure.
Figure 9:
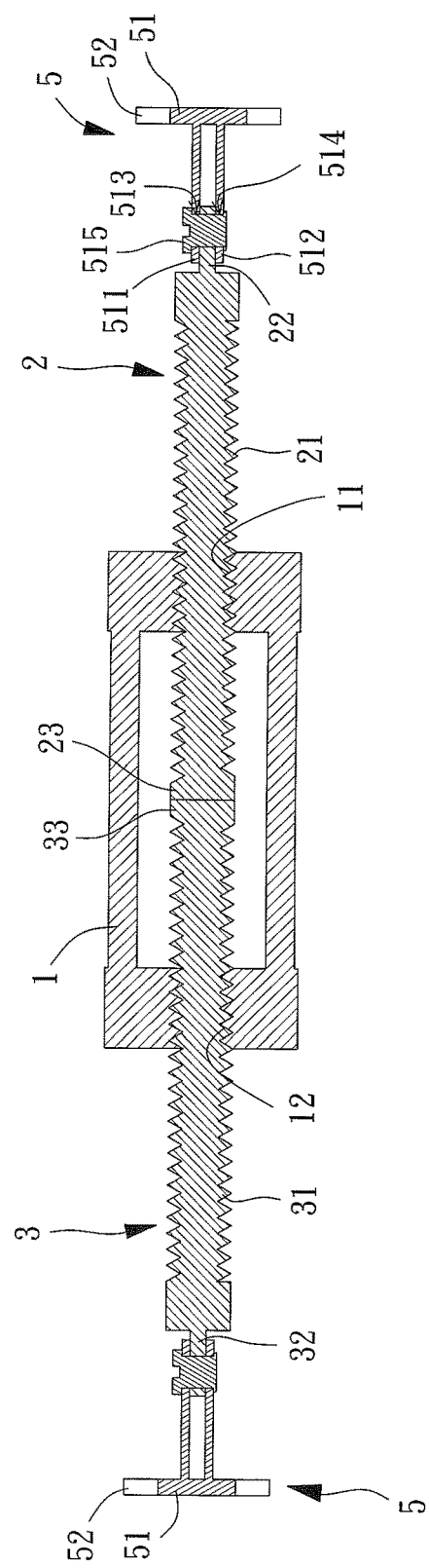
FIG. 9 is a cross sectional view of the mandibular fixation device of the second embodiment of the disclosure.

FIGS. 8 and 9 show a mandibular fixation device according to a second embodiment of the disclosure. The second embodiment of the disclosure is substantially the same as the first embodiment except that the second screw rod 3 has the same structure as the first screw rod 2. In the second embodiment, the first stopper portion 23 of the first screw rod 2 has a flat end face, and the second stopper portion 33 of the second screw rod 3 also has a flat end face. Based on this, the first screw rod 2 and the second screw rod 3 can be securely coupled with each other when they are in contact with each other. As such, the surgeon will be able to know when to stop turning the sleeve 1, which also prevents deformation and displacement of the first screw rod 2 and the second screw rod 3.

The mandibular fixation device in this embodiment is more suitable for use in a situation where it is not required to largely adjust the distance between the first screw rod 2 and the second screw rod 3. In addition, since the first screw rod 2 and the second screw rod 3 have the same structure, it is not required to separately manufacture and pack the first and second screw rods 2 and 3. It is also not necessary to classify the first and second screw rods 2 and 3 during the assembly thereof. Advantageously, convenient manufacturing, warehousing and assembly can be provided.

Based on the above, the mandibular fixation device of the disclosure can efficiently and accurately position the mandible of the patient with a proper positioning member according to the condition of mandible (e.g. depending on the degree of injury to the mandible, whether the patient has no teeth, and whether the patient has teeth but the tooth gaps are larger than normal). Thus, the efficiency in retaining the mandible of the patient is largely improved, permitting the surgeon to focus on the reconstruction of the mandible. Thus, the surgeon does not need to spend a lot of effort and time in retaining the mandible of the patient. This not only reduces the complexity of the surgery and the surgery time, but also ensures a proper positioning effect of the mandible. As such, the mandible of the patient can remain in a normal position after the surgery, increasing the confidence of the patient in socialization.

In the mandibular fixation device, if the positioning member is a dental ring, the fixation process of the mandible will not create any additional wound in the mouth of the patient. If the positioning member is a bone plate, although the use of the bone nails creates some wounds, the quantity of the created wounds is still much smaller than that created by the conventional approach which requires a bone nail to be nailed into each of the teeth gaps. This reduces not only the risk of infection but also the number of times the surgeon has to check the root and nerve of the tooth (to ensure the root and nerve of the tooth are not hurt by the bone nail). Thus, the mandibular fixation device of the disclosure as a whole can significantly increase the convenience and efficiency in operation. Furthermore, the mandibular fixation device of the disclosure does not require steel wires, and, therefor, the patient and surgeon will not be hurt by the steel wires, improving the safety of the maxillary fixation device.

Although the disclosure has been described in detail with reference to its presently preferable embodiments, it will be understood by one of ordinary skill in the art that various modifications can be made without departing from the spirit and the scope of the disclosure, as set forth in the appended claims.

What is claimed is:

1. A mandibular fixation device comprising:
   a sleeve having two ends respectively provided with a first screw hole and a second screw hole, wherein the first screw hole has a spiral direction opposite to a spiral direction of the second screw hole;
   a first screw rod having a first threaded portion and a first assembly portion, wherein the first threaded portion is threadedly engaged with the first screw hole, wherein the first assembly portion is located outside of the sleeve;
   a second screw rod having a second threaded portion and a second assembly portion, wherein the second threaded portion is threadedly engaged with the second screw hole, wherein the second assembly portion is located outside of the sleeve; and
   two positioning members coupled with the first and second assembly portions, respectively, wherein each of the two positioning members comprises a rotating member, wherein the rotating member comprises an upper screwing tab and a lower screwing tab, wherein the upper screwing tab has a through-hole, wherein the lower screwing tab has a screwing hole, wherein the first assembly portion of the first screw rod or the second assembly portion of the second screw rod is in a form of a protruding ring and extends into a space between the upper screwing tab and the lower screwing tab, and wherein a screw extends through the through-hole of the upper screwing tab and the first or second assembly portion, and is threadedly engaged with the screwing hole of the lower screwing tab.

2. The mandibular fixation device as claimed in claim 1, wherein the first screw hole is coaxial with the second screw hole.

3. The mandibular fixation device as claimed in claim 1, wherein the first screw hole has a same thread pitch as the second screw hole.

4. The mandibular fixation device as claimed in claim 1, wherein the sleeve has a central portion in a form of a hexagonal prism.

5. The mandibular fixation device as claimed in claim 1, wherein each of the two positioning members further comprises a ring body, wherein the rotating member comprises a first end that is fixed to the first assembly portion of the first screw rod or the second assembly portion of the second screw rod, and wherein the rotating member comprises a second end rotatably connected to the ring body.

6. The mandibular fixation device as claimed in claim 5, wherein the ring body is in a form of a C-shaped ring having an opening.

7. The mandibular fixation device as claimed in claim 1, wherein the first assembly portion is mounted to one of two axial ends of the first screw rod, wherein the first screw rod has a maximal diameter between the first threaded portion and another of the two axial ends of the first screw rod, wherein the second assembly portion is mounted to one of two axial ends of the second screw rod, wherein the second screw rod forms a channel in an open state at another of the two axial ends of the second screw rod, and wherein the channel has a minimal diameter larger than the maximal diameter of the first screw rod.

8. The mandibular fixation device as claimed in claim 1, wherein the first and second screw rods have a same structure.

9. The mandibular fixation device as claimed in claim 8, wherein the first assembly portion is mounted to one of two axial ends of the first screw rod, wherein another of the two axial ends of the first screw rod forms a first stopper portion, wherein the first threaded portion is located between the first assembly portion and the first stopper portion, and wherein the first stopper portion has a flat end face.

\* \* \* \* \*